United States Patent [19]
Hock et al.

[11] Patent Number: 5,561,063
[45] Date of Patent: *Oct. 1, 1996

[54] RECOMBINANT HUMAN CYTOMEGALOVIRUS CONTAINING FOREIGN GENE

[75] Inventors: Lisa J. Hock, La Jolla; Mark D. Cochran, Carlsbad; Richard D. Macdonald, San Diego, all of Calif.

[73] Assignee: Syntro Corporation, Lenexa, Kans.

[*] Notice: The term of this patent shall not extend beyond the expiration date of Pat. No. 5,273,876.

[21] Appl. No.: 164,220

[22] Filed: Dec. 9, 1993

Related U.S. Application Data

[63] Continuation of Ser. No. 599,270, Oct. 16, 1990, Pat. No. 5,273,876, which is a continuation of Ser. No. 67,375, Jun. 26, 1987, abandoned.

[51] Int. Cl.$^6$ ............................ C12N 15/86; C12N 7/01; C12N 15/00; C12N 15/11
[52] U.S. Cl. ........................ 435/320.1; 435/172.3; 435/235.1; 536/23.1; 536/23.7; 536/24.1
[58] Field of Search ........................ 435/172.3, 320.1, 435/235.1; 536/23.1, 23.7, 24.1

[56] References Cited

U.S. PATENT DOCUMENTS 4,707,357  11/1987  Dame ........................................ 424/88

OTHER PUBLICATIONS

Foecking et al, Gene 45:101–105 (1986).
Mocarski et al., Proc. Natl. Acad. Sci., 82:1266–1270 (1985).

Primary Examiner—Nancy T. Vogel
Attorney, Agent, or Firm—John P. White

[57] ABSTRACT

The present invention provides a virus comprising a DNA sequence essential for replication of a human cytomegalovirus and at least one foreign DNA sequence adapted for expression in a host. The foreign DNA sequence may encode a human immunodeficiency virus anti-sense mRNA sequence or an antigenic polypeptide, e.g., a malarial surface antigen.

Also provided are therapeutic compositions and vaccines which comprise the novel viruses of the present invention.

12 Claims, 8 Drawing Sheets

HCMV (Towne)

Figure 6

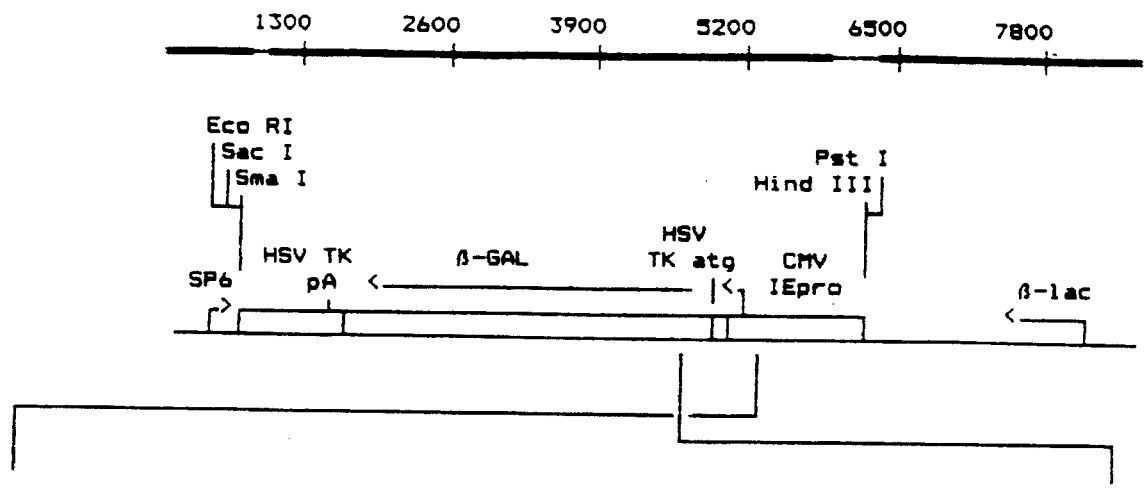

GGC ACC AAA ATC AAC GGG ACT TTC CAA AAT GTC GTA ACA ACT CCG CCC CAT TGA CGC

AAA TGG GCG GTA GGC GTG TAC GGT GGG AGG TCT ATA TAA GCA GGG GGA TCC TCT AGA
                  TATA    Bam HI Xba I

CAP?
 Sal I Pst I               Bgl II
GTC GAC CTG CAG CGA CCC GCT TAA CAG CGT CAA CAG CGT GCC GCA GAT CTT GGT GGC
CMV IE <⌐  L> HSV TK

GTG AAA CTC CCG CAC CTC TTC GGC CAG CGC CTT GTA GAA GCG CGT ATG GCT TCG TCG
                         Met Ala Ser Ser
Bam HI                      HSV TK <⌐
GAT CCC GTC GTT TTA CAA CGT CGT GAC TGG GAA AAC CCT GGC GTT ACC CAA CTT AAT
Asp Pro Val Val Leu Gln Arg Arg Asp Trp Glu Asn Pro Gly Val Thr Gln Leu Asn
  L> ECO β-GAL

CGC CTT GCA GCA CAT CCC CCT TTC GCC AGC TGG CGT AAT AGC GAA GAG GCC CGC ACC
Arg Leu Ala Ala His Pro Pro Phe Ala Ser Trp Arg Asn Ser Glu Glu Ala Arg Thr

RECOMBINANT HUMAN CYTOMEGALOVIRUS CONTAINING FOREIGN GENE

This application is a continuation application of U.S. Ser. No. 07/599,270, filed Oct. 16, 1990, now allowed, U.S. Pat. No. 5,273,876, which is a continuation of U.S. Ser. No. 07/067,375, filed Jun. 26, 1987, now abandoned.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

Human cytomegalovirus (HCMV) belongs to the animal herpesvirus group. The cytomegaloviruses occupy a special subfamily of the Herpesviridae called the Beta-herpesvirinae. Viruses belonging to this group exhibit narrow host range, long duration of the replication cycle with slowly progressing lytic foci in cell culture, and frequently show enlarged cells (cytomegalia) both in vitro and in vivo. The viruses also have a genomic organization (an arrangement of genes) which is distinct from other herpesvirus groups. These characteristics show that cytomegaloviruses are distinct from herpesviruses in other subfamilies (1). Accordingly, what is known and described in the prior art regarding other herpesvirus subfamilies does not pertain a priori to members of the cytomegalovirus subfamily.

HCMV occurs widely in the human population, e.g., approximately 60% of humans have serological evidence of infection by HCMV by adulthood. The infections occur through direct transmission by contact, often through mother's milk. The infection is usually asymptomatic, and HCMV has a reputation for being a very benign pathogen. Serious complications arise in two instances. Fetuses that are infected in utero by passage of HCMV from the mother (who herself is suffering a primary infection) can become infected and be born with "cytomegalic inclusion" disease. This is a serious HCMV infection, indicated by the excretion of large amounts of HCMV in the urine, and often leads to congenital defects involving sensorineural loss, e.g., hearing or psychomotor development, and retardation. The other instance involves any immunosuppressed individual, e.g., someone on immunosuppresive drugs, an individual suffering a congenital immunodeficiency, or an individual suffering an acquired immunodeficiency, e.g., AIDS. Because of the wide spread presence of HCMV, these individuals frequently suffer from a generalized HCMV infection which they are unable to combat immunologically. These two instances of HCMV diseases contribute a relatively large disease burden for which there is little or no therapy (2).

Two different HCMV strains have been tested as vaccines. The first test employed the AD-169 strain of HCMV given to healthy volunteers as described in (3). The test was successful with transient development of complement-fixing antibodies and little untoward side effects except a delayed local reaction at the site of injection. The virus was again tested by another group who confirmed the previous results and showed that immunological responses were maintained for at least one year (4). In an independent vaccine effort, the Towne strain of HCMV was grown in tissue culture for 125 passages (Towne-125) and tested as a candidate live virus vaccine (5). The results of the Towne-125 administration paralleled those of AD-169 administration; antibody responses were evident in healthy human volunteers, and a local delayed reaction occurred at the site of injection (6, 7). A prospective study was undertaken with the Towne-125 strain in patients with end-stage renal failure who were candidates for transplants and hence immunosuppressive therapy (8). All seronegative vaccinates developed antibody and none had adverse side-effects except for local reactions, and no vaccine-related problems were identified in the interval after transplantion. However six of the nine vaccinates did excrete HCMV in their urine after transplantation and immunosuppressive therapy, albeit this was wild type and not vaccine strain. Thus the vaccination did not protect fully against infection or re-activation of HCMV, but statistically the patients were better off for having been vaccinated. In a direct safety comparison between the Towne-125 strain and a wild type Toledo-1 strain in healthy seronegative volunteers, the Toledo-1 strain was shown to induce laboratory abnormalities or mild mononucleosis only, while the Towne-125 strain showed no adverse effects except for delayed local reactions at the site of injection (9). These studies show that existing strains of HCMV have a high degree of safety, even in immunosuppressed patients, which may be improved by reducing the delayed reactions at the site of injection.

The present invention concerns the use of HCMV as a vector for the delivery of vaccine antigens and therapeutic agents to humans. The following properties of HCMV support this rationale: HCMV is ubiquitous in nature; HCMV has benign effects in healthy individuals; an HCMV strain exists which appears safe for immunocompromised individuals; and the target population for an HCMV-delivered therapeutic agent is likely to have been exposed to wild type HCMV and therefore should not have an increased risk burden from the vector. Accordingly an attenuated HCMV is an excellent candidate for a vital vector delivery system, having little intrinsic risk which must be balanced against the benefit contributed by the vector's vaccine or therapeutic properties.

The prior art for this invention stems first from the ability to clone and analyze DNA while in bacterial plasmids. The techniques that are available for the most part are detailed in Maniatis et al. (10). This publication teaches state of the art general recombinant DNA techniques.

Among the herpesviruses, only four herpesviruses (herpes simplex of humans, herpes saimiri of monkeys, pseudorabies virus and varicella-zoster virus) have been engineered to contain foreign DNA sequences previous to this disclosure. The earliest work on the genetic manipulation of herpes simplex involved the rescue of temperature sensitive mutants of the virus using purified restriction fragments of DNA (11). This work did not involve cloning of the DNA fragments nor the purposeful creation of deletions nor insertions of foreign DNA fragments into the viral genome. The first use of recombinant DNA to manipulate herpes simplex virus involved cloning a piece of DNA from the L-S junction region into the unique long region of the DNA, specifically into the thymidine kinase gene (12). This insert was not a foreign piece of DNA, rather it was a naturally-occurring piece of herpesviruses DNA that was duplicated at another place in the genome. This piece of DNA was not engineered to specifically express any protein, and thus it did not teach how to express protein in herpesviruses. The manipulation of herpes simplex next involved the creation of deletions in the virus genome by a combination of recombinant DNA and thymidine kinase selection. The first step was to make a specific deletion of the thymidine kinase gene (13). The next step involved the insertion of the thymidine kinase gene into the genome at a specific site, and then the thymidine kinase gene and the flanking DNA at the new site were deleted by a selection against thymidine kinase (14). In this manner herpes simplex alpha-22 gene has been deleted. (14). In the most recent refinement of this technique, a 15,000 bp sequence of DNA has been deleted from the internal repeat of herpes simplex virus (15).

The insertion of genes that encode protein into herpesviruses have involved a number of cases: the insertion of herpes simplex glycoprotein C back into a naturally occurring deletion mutant of this gene in herpes simplex virus (16); the insertion of glycoprotein D of herpes simplex type 2 into herpes simplex type 1 (17), again with no manipulation of promoter since the gene is not really "foreign"; the insertion of hepatitis B surface antigen into herpes simplex virus under the control of the herpes simplex ICP4 promoter (18); and the insertion of bovine growth hormone into herpes saimiri virus with an SV40 promoter that in fact didn't work in the system (an endogenous upstream promoter served to transcribe the gene) (19). Two additional cases of foreign genes (chicken ovalbumin gene and Epstein-Bart virus nuclear antigen) have been inserted into herpes simplex virus (20), and glycoprotein X of pseudorabies virus has been inserted into herpes simplex virus (21).

More recently, the herpes simplex virus TK gene and the tissue plasminogen activator gene have been inserted into pseudorabies virus (PCT International Publication No. WO87/00862), and an Epstein-Bart virus glycoprotein antigen has been inserted into varicella-zoster virus (22).

These examples of insertions of foreign genes into herpesviruses do not include an example from the cytomegalovirus subfamily. Thus they do not teach methods to genetically engineer cytomegaloviruses, i. e., where to make insertions and how to get expression.

The idea of using live viruses as delivery systems for antigens has a relatively long history going back to the first live vaccine. The antigens were not "foreign" but were natural components of the live vaccines. The use of viruses as a vector for the delivery of "foreign" antigen in the modern sense became obvious with the vaccinia virus recombinant studies. There vaccinia was the vector and various antigens from other diseases were the "foreign" antigens, and the vaccine was created by genetic engineering. While the concept became obvious with these disclosures, what was not obvious was the answer to a more practical question of which are the best candidate virus vectors. In answering this question, details of the pathogenicity of the virus, its site of replication, the kind of immune response it elicited, the potential for it to express foreign antigens, its suitability for genetic engineering, its probability of being licensed by the FDA, etc, are all factors in the selection. For example, a vital vector carrying a therapeutic agent needs to target the correct cell type to deliver the therapeutic agent. The prior art does not teach these utility questions.

Furthermore, the obvious use of vaccinia virus to carry foreign antigens does not extend to its use in the delivery of therapeutic agents. Moreover, the use of any herpesvirus as a vector for therapeutic agents has equally not been pursued in the prior art.

The prior art relating to the use of viruses as therapeutic vectors involves members of the retrovirus family. These viruses are distinctive because they integrate into the host cell genome during infection, and they can be engineered to deliver foreign genes that potentially could cure genetic diseases. This concept involving retroviruses cannot be extended to any other virus family by analogy because of the unique nature of the retrovirus replication cycle.

The nature of the therapeutic agent that is to be delivered by a vital vector of the present invention must be a biological molecule that is a by-product of cytomegalovirus replication. This limits the therapeutic agent in the first analysis to either DNA, RNA, or protein. There are examples of therapeutic agents from each of these classes of compounds in the form of anti-sense DNA, anti-sense RNA, interferon-inducing double stranded RNA, and numerous examples of protein therapeutics, from hormones, e.g., insulin, to lymphokines, e.g., interferons and interleukins, to natural opiates. The discovery of these therapeutic agents and the elucidation of their structure and function does not make obvious the ability to use them in a viral vector delivery system.

SUMMARY OF THE INVENTION

The present invention provides a virus comprising a DNA sequence essential for replication of a human cytomegalovirus and at least one foreign DNA sequence adapted for expression in a host.

The present invention also provides the novel plasmids designated pSY1157 and pSY1159.

Legend:

L=long segment of the genome

S=short segment of the genome

J=junction

B=BamHI

E=EcoRI

P=PstI

S=SacI

X=SbaI

Xh=XhoI

IE=site of the immediate early promoter

↑=restriction sites targeted as potential insertion site

↑=restriction sites suitable for insertion ♦for foreign genes

Figure 2:
Figure 2:
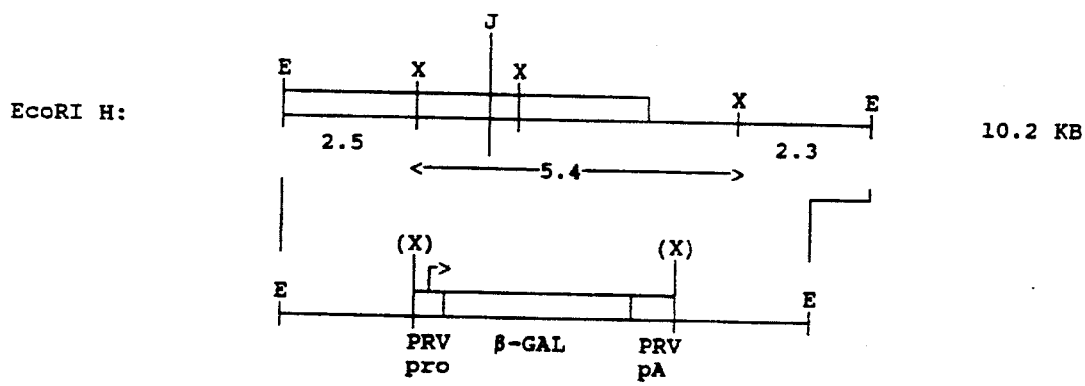
Figure 2:
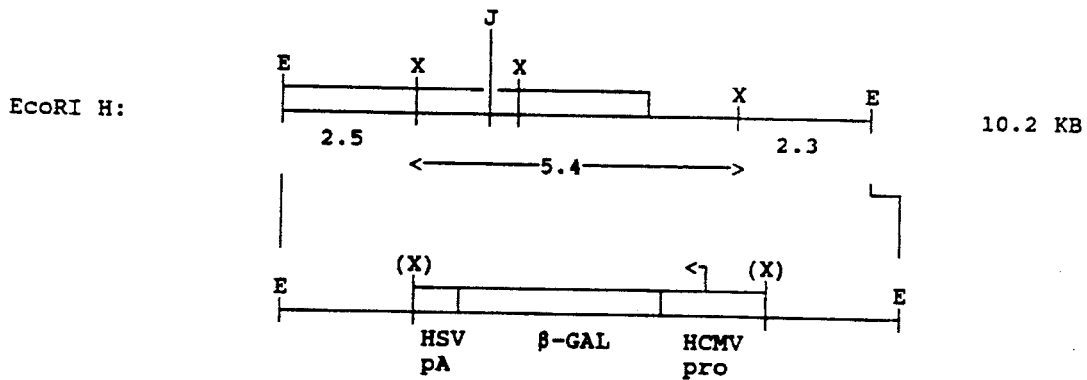

FIG. 2 schematically shoos the insertion of pRVgpX/beta-gal into the EcoRI H fragment of Towne HCMV at the XhoI deletion, to generate homology vector pSY920. Also shown is the insertion of HCMV IE/beta-gal into the EcoRI H fragment of Towne HCMV at the XhoI deletion to generate homology vector pSY930.

Legend:

L=long segment

S=short segment

J=junction

Figure 3:
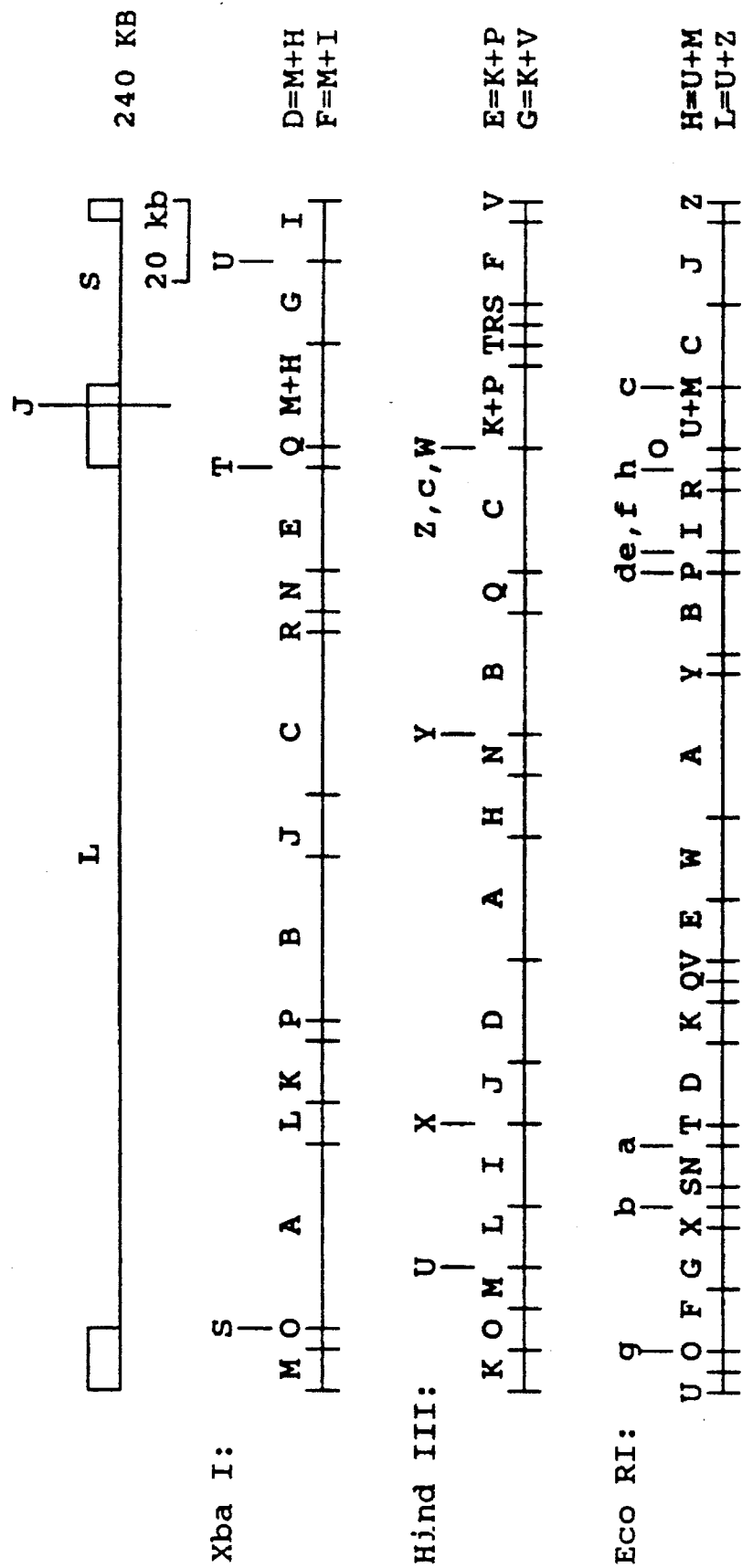
Figure 3B:
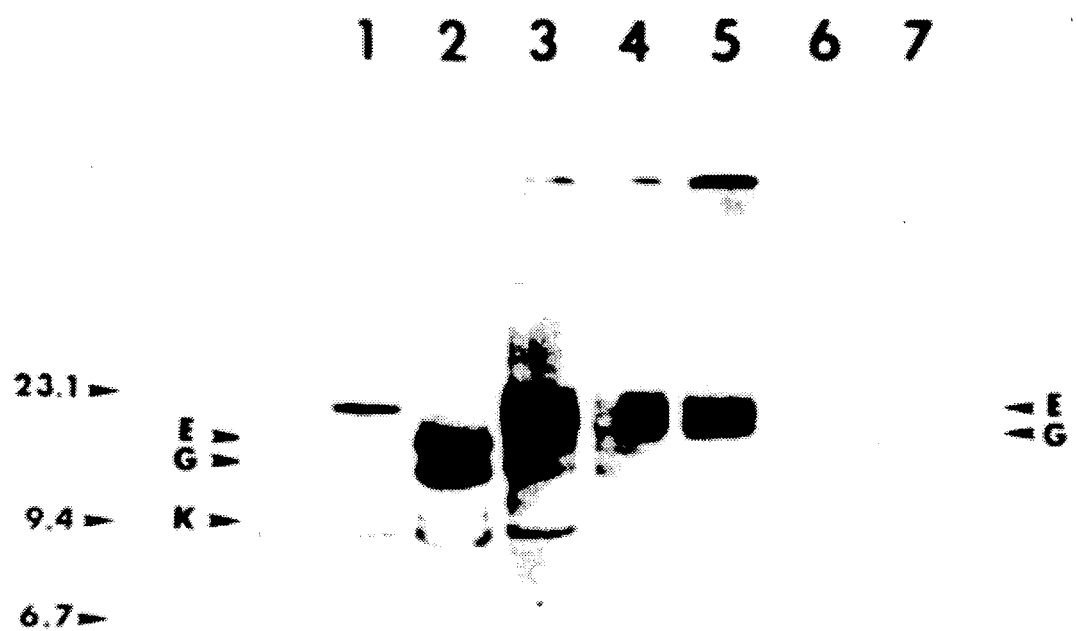
Figure 3C:
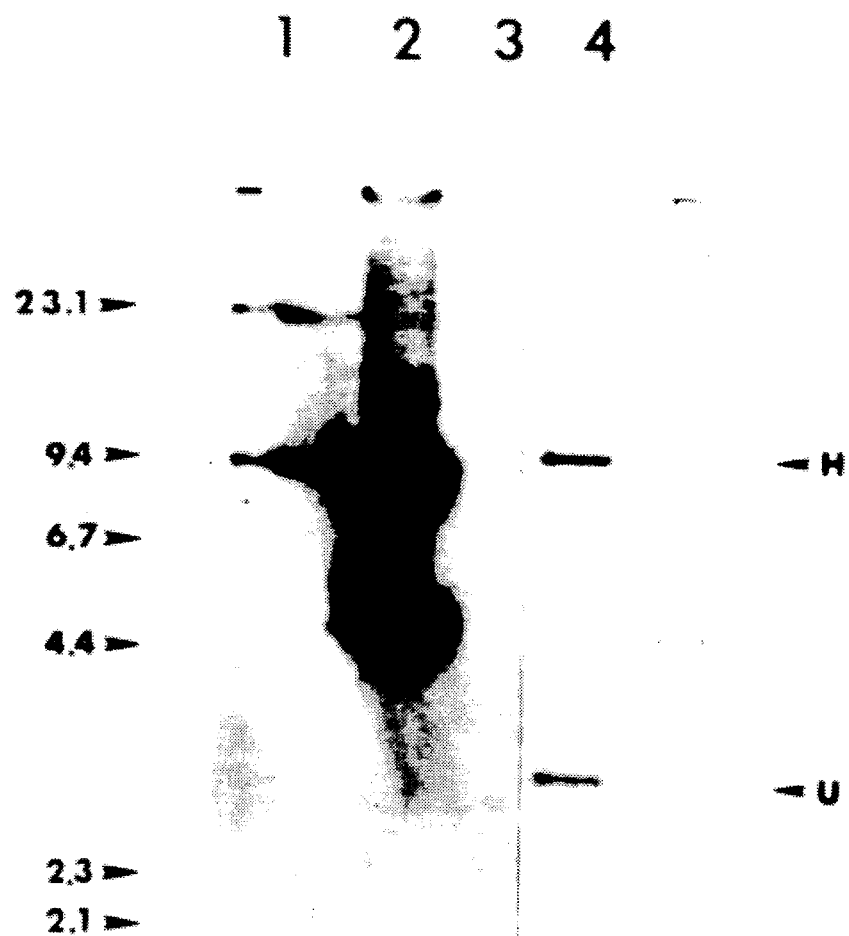

FIG. 3 is up of FIGS. 3A, 3B and 3C. FIG. 3A shows the HCMV (Towne) genome organization and XbaI, HIndlII, and EcoRI restriction enzyme maps.

Legend:

L=long segment

S=short segment

J=junction

FIG. 3B shows the confirmation of S-HCMV-001 structure by Southern blot analysis. Lanes 1 and 7 contain molecular weight markers. Lane 2 represents HCMV Towne DNA digested with HindIII and probed with XbaI M DNA. Lane 3 and half of Lane 4 represent the HCMV/beta-gal recombinant (S-HCMV-001) digested with HindIII and probed with beta-gal DNA. Lane 6 represents HCMV Towne DNA digested with HindIII and probed with beta-gal DNA.

FIG. 3C shows the confirmation of recombinant virus (beta-gal insert at the XhoI deletion) structure by Southern blot analysis. Lane 1 contains molecular weight markers. Lane 2 represents plasmid pSY1112 digested with EcoRI and probed with plasmid pSY844. Lane 3 represents HCMV Towne DNA digested with EcoRI and probed with beta-gal DNA. Lane 4 represents HCMV/beta-gal recombinant virus digested with EcoRI and probed with beta-gal DNA.

Figure 4:
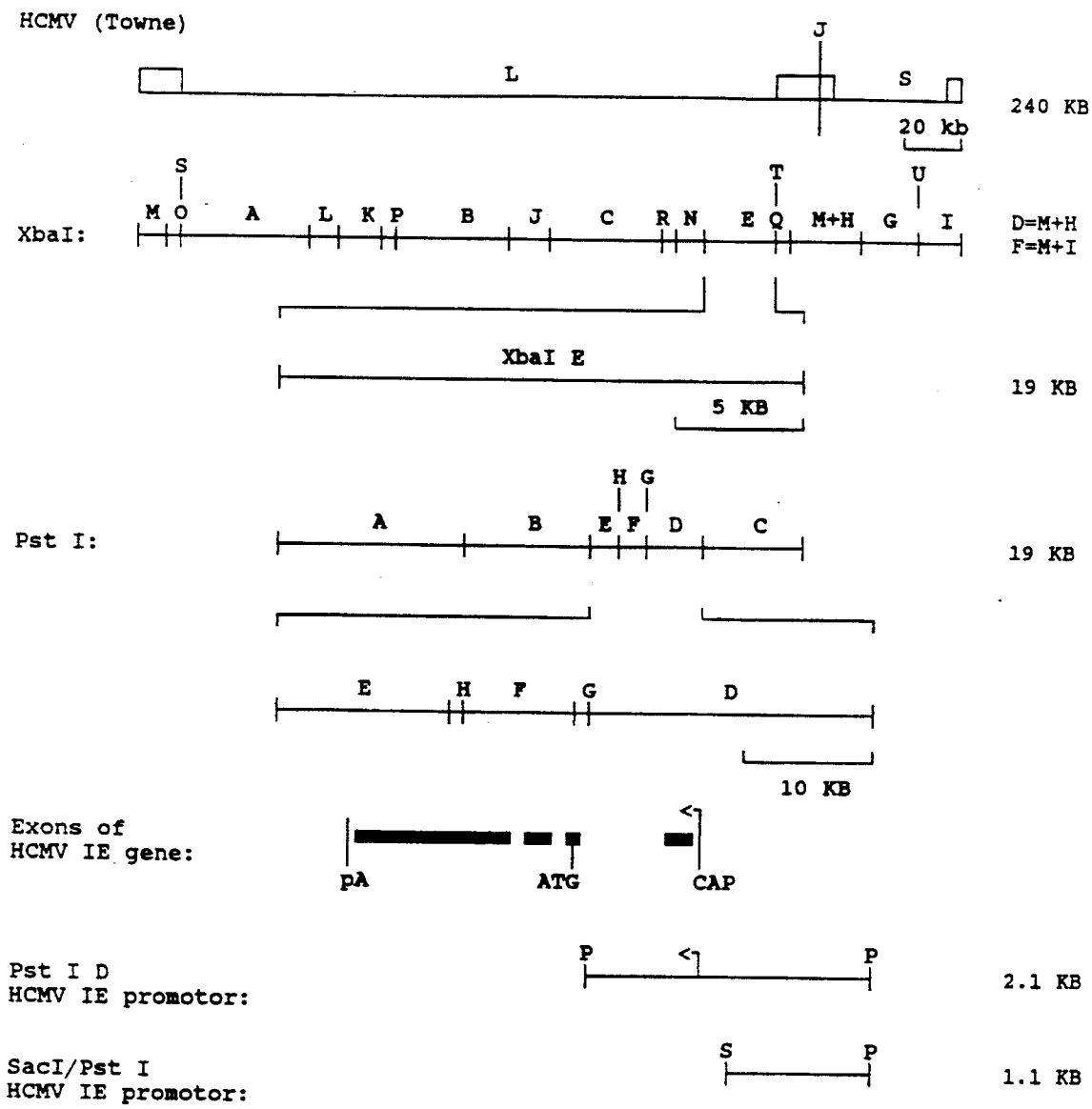

FIG. 4 schematically shows the cloning of the 2.1 kb PstID fragment and the 1.1 kb PstI to SacI fragment from Towne HCMV.

Legend:

L=long segment of the genome

S=short segment of the genome

J=junction

P=PstI

S=SacI

Figure 5:
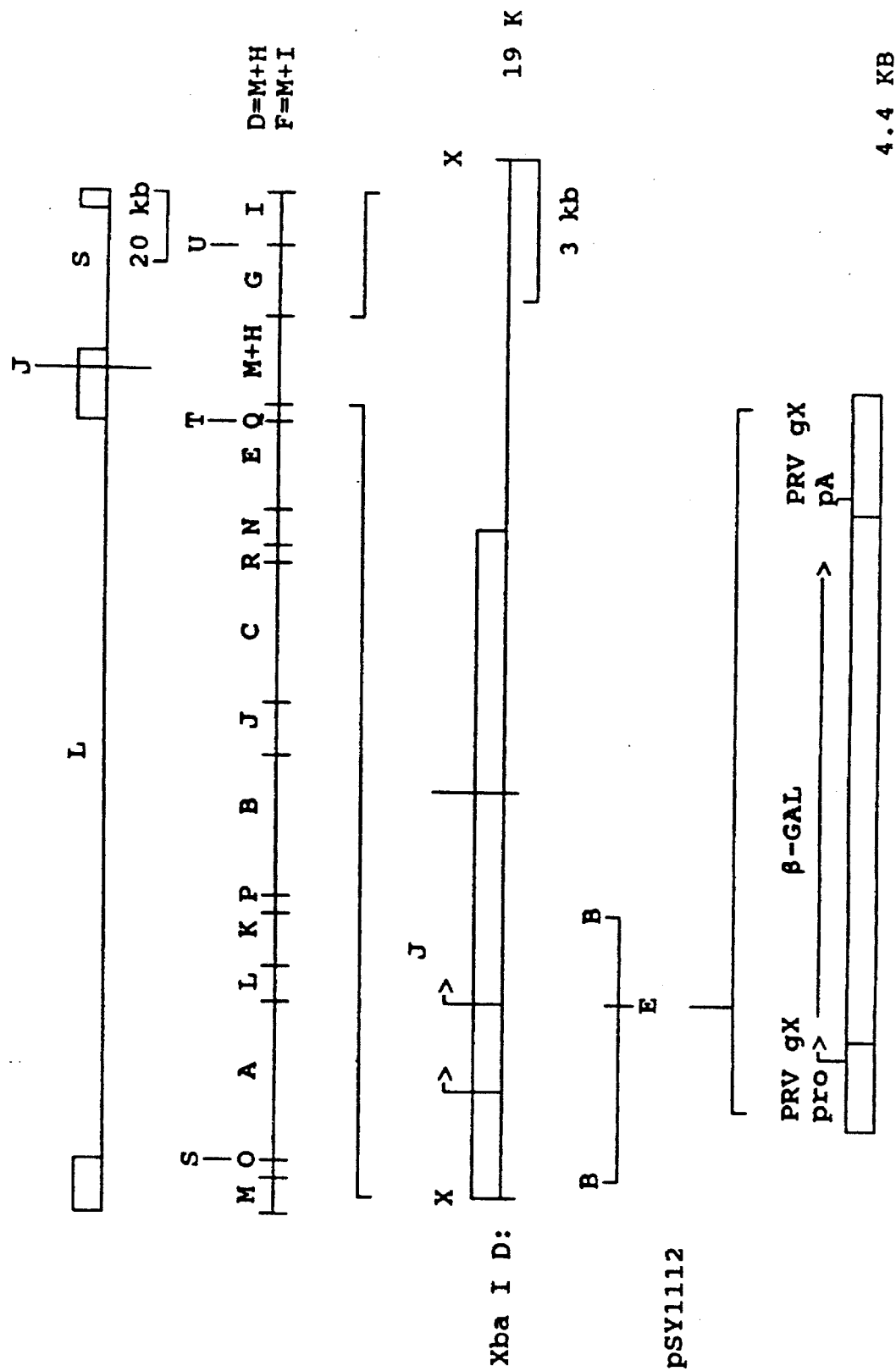

FIG. 5 schematically shows the insertion of PRV gpx/beta-gal into the 5.4 kb BamHI fragment of Towne HCMV at the RI site to generate homology vector pSY1112.

Legend:

L=long segment of the genome

S=short segment of the genome

J=junction

B=BamHI

E=EcoRI

X=XbaI

FIG. 6 shows the insertion of the HCMV IE PstI to SacI fragment at the cap site of the HSV TK segment, to generate the HCMV IE/beta-gal construct pSY1132. The DNA and amino acid sequences of part of this fusion are also shown.

DETAILED DESCRIPTION OF THE INVENTION

The present invention provides a virus comprising a DNA sequence essential for replication of a human cytomegalovirus and at least one foreign DNA sequence adapted for expression in a host. In one embodiment of the invention, the DNA sequence essential for replication of the human cytomegalovirus is derived from a naturally-occurring human cytomegalovirus. In another embodiment of the invention, the virus is auttenuate. Furthermore, the foreign DNA sequence adapted for expression in a host may encode a human immunodeficiency virus anti-sense mRNA sequence. This DNA sequence may comprise the DNA sequence which encodes a human immunodeficiency virus anti-sense mRNA sequence and is shown in FIG. 6.

Additionally the foreign DNA sequence may encode an antigenic polypeptide. In one embodiment of the invention, the foreign DNA sequence encodes a malarial surface antigen. In another embodiment of the invention, the foreign DNA sequence encodes beta-galactosidase.

Figure 1:
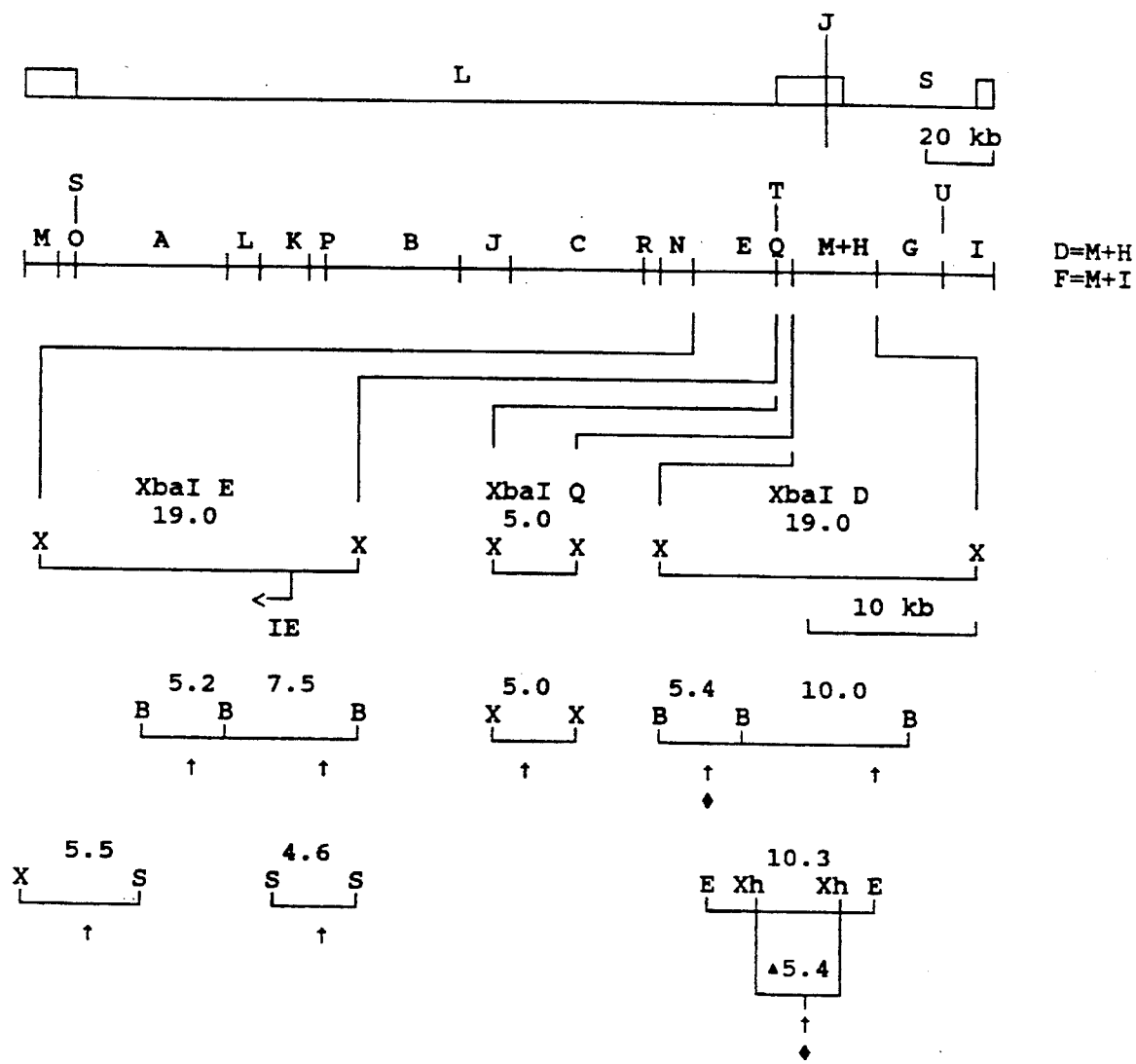
FIG. 1 shows the HCMV (Towne) genome organization. An XbaI restriction enzyme map, with cloning and insertion strategy illustrated, is also shown.

In still another embodiment of the invention, the foreign DNA sequence is inserted into the human cytomegalovirus at the EcoRI restriction endonuclease cleavage site of the 5.4 kb BamHI fragment shown in FIG. 1. In yet another embodiment of the invention, the foreign DNA sequence is inserted into the human cytomegalovirus so as to replace the 5.4 kb XhoI deletion fragment of the EcoRI fragment shown in FIG. 2.

In another embodiment of the invention, the foreign DNA sequence is adapted for expression by an endogenous upstream human cytomegalovirus promoter. The endogenous upstream human cytomegalovirus promoter may be the immediate early promoter.

Furthermore the foreign DNA sequence may be adapted for expression by a heterologous upstream promoter. In one embodiment of the invention, the heterologous upstream promoter is the pseudorabies gpX promoter. In another embodiment of the invention, the heterologous upstream proreoteris the human cytomegalovirus immediate early promoter.

The present invention also provides a plasmid designated pSY1157. This plasmid has been deposited with the American Type Culture Collection (ATCC), Rockville, Md. 20852, on Jun. 25, 1987, in the *E. coli* host cell JM101 under ATCC Accession No. 67452. Also provided by the present invention is a plasmid, designated pSY1159, which has been deposited with the ATCC, Rockville Md. 20852 Jun. 25, 1987, in the *E. coli* host cell JM101 under ATCC Accession No. 67453. The human cytomegalovirus Towne strain, S-HCMV-001, has been deposited with the American Type Culture Collection, Rockville, Md. 20852, on Jun. 25, 1987, under ATCC accession number VR2174.

The present invention al so provide s a therapeutic composition comprising an attenuated virus including a DNA sequence essential for replication of a human cytomegalovirus and a foreign DNA sequence which encodes a human immunodeficiency virus anti-sense mRNA sequence, and a pharmaceutically acceptable carrier. Pharmaceutically acceptable carriers are known in the art to which the present invention pertains and include, but are not limited to, 0.01–0.1M, preferably 0.05M, phosphate buffer or 0.8% saline. This therapeutic composition may be used to treat a subject infected with human immunodeficiency virus by administering to the subject an effective human immunodeficiency virus treating amount of the therapeutic composition provided herein.

Also provided by the present invention is a vaccine comprising an attenuated virus including a DNA sequence essential for replication of a human cytomegalovirus and at least one foreign DNA sequence adapted for expression of an antigenic polypeptide, and a pharmaceutically acceptable carrier. This vaccine may be used to immunize a human subject against a disease by administering to the subject an effective immunizing amount of the vaccine provided herein.

In one embodiment of the invention, the virus of the vaccine includes a foreign DNA sequence which encodes a malarial surface antigen. This vaccine may be used to immunize a human subject against malaria.

The viruses, therapeutic compositions, vaccines and methods for immunizing and treating human subjects provided by the present invention are based upon the ability to construct novel viruses from wild type or attenuated human cytomegaloviruses. These novel viruses and methods for their preparation will be better understood by reference to the following experiments and examples which are provided for purposes of illustration and are not to be construed as in any way limiting the scope of the present invention, which is defined by the claims appended hereto.

EXAMPLES

Example 1 a. Human Fibroblast Cultures

Fibroblasts from human embryonic lung and foreskins were compared for their ability to support the growth of the Towne strain of HCMV. We have examined W138 cells (human embryonic lung, passage 24); Flow 5000 (human embryonic fibroblasts, passage 16); Flow 7000 (human foreskin fibroblasts, passage 17); and EC100 cells (human foreskin fibroblasts, passage 10). Due to the superior quality of HCMV plaques on foreskin fibroblasts (HFF) and the lower passage number of the available cells, HFF cells were chosen for further work. Flow 5000, Flow 7000, EC100, or primary cultures prepared in our lab all gave satisfactory results. Flow 7000 cells were obtained from Flow Laboratories at passage 17 and used for most of the experiments reported here, although recently we have begun to use EC100 cells which have a lower passage number. The cells are routinely cultured in minimal essential medium (MEM) containing 10% fetal bovine serum, 2 mM L-glutamine, and 100 units/ml of pen-strep. Cultures are split 1:2 by trypsinization and resuspension in fresh medium. We refer to the various human foreskin fibroblast cells as HFF regardless of commercial origin as they are essentially interchangeable.

b. Infection with HCMV

HFF are infected when they reach 80% confluence at a multiplicity of infection (MOI) of 0.01 to prevent the formation of defective interfering particles. When the cells demonstrate 100% cytopathic effect, they are harvested, centrifuged and resuspended in a 1:1 mixture of growth medium and sterile skim milk (9% w/v dry skim milk in water). The cells are then sonicated on ice and stored at $-70°$ C. We routinely obtain titers of $10^8$ PFU/ml for Towne strain by this method. Strain AD169, which was provided by ATCC grows more slowly than Towne and reached titers of $10^7$ PFU/ml. A clinical isolate of HCMV, strain "Jerry", was obtained from Dr. Jay Nelson, Scripps Clinic and Research Foundation, La Jolla, Calif. This virus grows more slowly than Towne or AD169 and gives titers of $10^6$ PFU/ml.

c. Plaque Assay for HCMV

HFF are plated in 6-well Falcon dishes at 80% confluency. The next day, virus stocks are diluted $1:10^5$, $10^6$, and $10^7$ in growth medium. From these diluted samples, 10 microliters are added to each well containing 1.5 ml of fresh medium containing 5% fetal bovine serum (FBS). Cell monolayers are examined with a microscope for the appearance of plaques consisting of rounded cells. For the Towne strain, these plaques can be quantitated 5–6 days post infection. For AD169, 10–12 days were required to see plaques, and for "Jerry" 12–14 days are necessary to distinguish plaques. Quantifiable dishes contain between 20 and 50 plaques.

d. Transfection with HCMV DNA

We use various methods to transfect vital DNA from a number of animal herpesviruses. We have tested these various methods to transfect HCMV DNA. It is our observation that HCMV DNA can transfect HFF cells by $CaCl_2$/DMSO and Polybrene/DMSO treatment but does not transfect by DEAE dextran/DMSO, $CaCl_2$/glycerol, nor $CaCl_2$/PEG treatments. In all cases, HCMV DNA was not CsCl purified and the DNA was transfected into HFF cells. As a control, pseudorabies virus DNA was also successfully transfected into HFF cells by $CaCl_2$/DMSO treatment but did not transfect by $CaCl_2$/glycerol, nor DEAE dextran/DMSO treatments.

We have compared the transfection assay in human fibroblast cells at various passage levels. For example, using the Polybrene/DMSO method, we observed plaques in Flow 5000 cells on day 10 post-transfection and plaques in Flow 7000 cells on day 6 post-transfection. Flow 7000 cells appear to produce plaques earlier than the Flow 5000 cells. In addition, the plaques in Flow 7000 cells are more compact. Because the plaques are more distinct, they are more easily picked. Therefore, lower passage HFF cells were chosen to use when transfecting HCMV DNA and screening recombinant viruses.

A transient expression system was used to determine that specific gene constructions were functional (see Section 1.4). In these assays, it was possible to use a standard transfection protocol to introduce plasmid DNA into HFF cells ((25), Section 1.4). However, when HCMV recombinants were produced by homologous recombination between plasmids and vital DNA, the polybrene method mentioned above was necessary in order to obtain satisfactory results using the much larger HCMV DNA. In this procedure, HFF cells were plated into 60 mM dishes at 80% confluency and allowed to attach. The cells were pre-treated with 4 micrograms/ml polybrene in growth medium overnight (18–20 hrs) at $37°$ C. This medium was removed and replaced with 1 ml of growth medium containing 12 micrograms/ml polybrene and the appropriate amount of HCMV DNA (see below). After adsorbing the DNA to the cells for 30 min. in the $37°$ C. $CO_2$ incubator, growth medium was added without polybrene and incubated an additional 3.5 hrs. The inoculum was replaced with 30% DMSO in Hank's Balanced Salt Solution (HBSS) for 4 min. at room temperature and then the cells were washed once with HBSS, fresh growth medium was added and incubation continued overnight. The following day the cells were re-fed with fresh growth medium and incubated until plaques formed.

Optimization Of DNA Concentration: After titering many stocks of HCMV DNA, we established that 1–2 micrograms of HCMV DNA is the optimum for our transfection assays.

With the polybrene/DMSO transfection experiments, we routinely obtained 1–15 plaques/1–2 micrograms HCMV DNA for each HCMV DNA preparation and saw no increase in the number of plaques by further increasing the amount of HCMV DNA.

Example 2

INFECTION OF OKT4$^+$LYMPHOCYTES WITH HCMV

The AIDS virus, HIV, has been shown to infect OKT4$^+$ helper T-lymphocytes (23). It is thought that this infection leads to the decrease in T4 lymphocytes observed in AIDS patients and is at least in part responsible for the immunodeficiency caused by this virus. The success of our strategy to deliver an AIDS antisense message with HCMV depends upon the ability of HCMV to infect T4 lymphocytes or other cell types permissive for HIV replication and to express the antisense message. The feasibility of this approach depends upon the ability of a recombinant HCMV to express a foreign gene in HIV permissive cells.

a. OKT4 Cell Culture

For the present experiments we have used HUT-78 cells (ATCC TIB161) as the prototype OKT4 cells. These cells grow in suspension and are maintained in RPMI medium containing 10% heat inactivated fetal bovine serum, 2 mM glutamine, and 100 units/ml pen-strep. We routinely use volumes of 20 mls contained in T-75 flasks standing on end. Since these cells condition their medium with Interleukin-2 (IL-2) (24), and other lymphokines, they are split about 1:3 to approximately $2 \times 10^5$ cells/ml every 2 days by dilution with fresh medium without centrifugation of the cells. They routinely reach densities approaching $10^7$ cells/ml under these conduit ions.

Frozen stocks were established by centrifuging the cells, resuspending them to about $5 \times 10^6$ cells/ml and 1 ml per ampule in RPMI containing 20% fetal calf serum, 2 mM glutamine, 100 units/ml pen-strep and 5% DMSO, freezing overnight at $-70°$ C. and storage in liquid nitrogen.

b. HCMV Infection

HUT-78 cells were cultured in RPMI medium containing 10% heat inactivated fetal bovine serum, 2 mM glutamine, 100 units/ml of pen-strep and 10 one-half maximal units/ml of IL-2. After six days in culture, the cells are pelleted by centrifugation and resuspended in a sufficient volume of stock virus prepared in HFF cells, so that the multiplicity of infection is 5. The mixture is then incubated at 37° C. for 3 hrs., diluted with RPMI, and the cells pelleted by centrifugation. The cells are then re-fed with fresh RPMI medium containing one-half maximal units of IL-2/ml or with a mixture of that medium and 50% medium previously conditioned by uninfected OKT4 cells.

Three assays were used to monitor the HCMV infection of HUT-78 cells:

1. Determination of beta-galactosidase activity following infection with the HCMV Towne strain containing the *E. coli* beta-gal gene. At various times after infection an aliquot of the infected culture is removed, centrifuged and beta-gal activity determined directly on the supernate and on the cleared cellular lysates. The cells were disrupted with 1% NP-40 in PBS and centrifuged to produce the lysates.
2. Determination of cell free virus titer. Infected HUT-78 cells are centrifuged and the virus titer in the supernate determined by plating 5, 50, 500 lambda aliquots in HFF cells. Plaques are quantitated by examination with a microscope. Results are expressed as virus titer per $1 \times 10^5$ HUT-78 cells.
3. Infectious center assay. This assay was used to determine the percentage of HUT-78 cells containing infectious virus. At various times after infection cells were removed, washed three times by centrifugation in fresh medium and resuspended in 1 ml of medium. Dilutions of $1:10^1$, $10^2$, $10^3$, $10^4$ were made in medium and added to a suspension of HFF cells ($1 \times 10^5$) which results in approximately 80% confluency when plated into Falcon 6-well dishes. The cells were mixed and plated. The cells were allowed to settle overnight. The next day, the medium was carefully removed and the cultures overlaid with 0.75% low-melting temperature agarose in medium MEM containing 5% fetal bovine serum, 2 mM glutamine, and 100 units/ml pen-strep. Cultures were incubated and examined for plaques. In the case of the beta-gal containing HCMV infections, blue plaques were determined following the addition of Bluogal as substrate.

Example 3

DELETION OF REGIONS OF HCMV TO BETTER ATTENUATE VIRUS AND LOCALIZE POSITIONS FOR INSERTION.

One of the primary objectives is to insert and express a gene coding for HIV anti-sense RNA into HCMV. We have identified sites on the HCMV genome where deletions and/or insertions of foreign genes can be made and which permit expression of foreign genes.

Construction of 9 HCMV Clones: Summary: A series of 9 regions of the HCMV genome were cloned into plasmid vectors in *E. coli*. Attempts were made to insert the marker enzyme *E. coli* beta-galactosidase (beta-gal) into the cloned HCMV DNA. To date, 2 constructions carrying the beta-gal insert have been made and confirmed (starred in tabulation presented below).

As diagrammed in FIG. 1, three larger fragments from repeat regions and the long unique regions of HCMV (Towne) were isolated and cloned. From these 3 larger fragments, smaller fragments were subcloned and used for insertion of beta-gal. Listed below are the larger cloned fragments and the subclones derived from these fragments. The size of the cloned HCMV fragment and the site of insertion is described.

Xba E Fragment, 19 kb, part of the long unique region

Five fragments were sub-cloned from the 19 kb Xba E fragment.

| SACl B | 5.5 kb | insert at the SalI site |
|---|---|---|
| BamHI B | 5.2 kb | insert at the SalI site |
| BamHI A | 7.5 kb | insert at the SalI site |
| sub-clone of BamHI A: | | |
| SAC C | | insert at the SalI site |
| sub-clone of SAC C: | | |
| Pst C | | insert at the SalI site |

2. Xba O Fragment: 4,8 kb, long internal repeat Insertion at MLUI site.
3. Xba D Fragment: 19 kb, long internal repeat, short internal repeat and part of unique short Three fragments were subcloned from the Xba D fragment:

| BamHI* | 5.4 kb | insert at RI site (successful insertion) |
|---|---|---|
| BamHI | 10 kb | insert at RI site |
| EcoRI H* | 10.2 kb | insert into 5.4 kb XhoI deletion (successful insertion) |

At the present time, we have the above 9 cloned fragments available for beta-gal insertion. Beta-gal was placed into the RI site of the 5.4 kb BamHI fragment from Xba D and into the 5.4 kb XhoI deletion from the EcoRI H fragment (10.2 kb) derived also from Xba D. These constructions are further detailed.

1.1 Construction of a homology vector, pSY920, for insertion into EcoRI H fragment using Pseudorabies gpX promoter:

The promoter of pseudorabies glycoprotein X (gpX) provided a convenient and active promoter to fuse to beta-gal. We have had some experience with this promoter which speeded the genetic constructions and which gave us confidence that it might function well in a heterologous system.

1.2 The beta-gal construction

Summary: The coding region of the glycoprotein X (gpX) gene of pseudorabies was deleted and replaced by the structural gene for *E. coli* beta-galactosidase. The resulting construct places beta-gal under the pseudorabies promoter control with the gpX poly A and termination signals. This construction is inserted into a derivative of pSP64 downstream from the SP6 promoter at the SalI site.

Constructions: The promoter for pseudorabies gpX lies in the BamHI #10 fragment and the bulk of the gene extends into the BamHI #7 fragment of the pseudorabies virus (PRV) genome. Both BamHI #10 and BamHI #7 were cloned and the BamHI #7 fragment was cut at the NdeI site, removing almost all of the coding region of gpX to the C terminus. The NdeI site was filled in. The BamHI to BalI fragment. of the *E. coli* beta-gal gene was inserted at the BamHI site of the gpX promoter fragment (BamHI #10) and the C terminal of gpX (Nde site of BamHI #7). The resulting construction fuses the gpX promoter and translational start in-frame to the betagal structural gene and provides the gpX termination and poly A signals. The entire construct resides on a 4.4 kb SalI fragment which was cloned into the multicloning site of pSP64 downstream from the SP6 promoter region to form plasmid pSY844.

1.3 Insertion of PRV gpX/Ybeta-gal into the EcoRI H fragment at the Xho I deletion The EcoRI H fragment (10.2 kb) includes part of the long internal repeat, the junction region, the entire short internal repeat and part of the unique short region (FIG. 1). This fragment was cloned and two internal XhoI fragments totalling 5.4 kb were removed. The deleted fragment includes part of the long internal repeat, the junction region, the short internal repeat and a fraction of the unique short region. The 4.4 kb SalI fragment carrying beta-gal (see 1.2 above) was ligated into the Xho I deletion site. The resulting construction flanks the beta-gal gene with HCMV sequences appropriate for insertion by homologous recombination into the HCMV virus (Homology vector, pSY920) (see FIG. 2).

1.4 Confirmation of a functional construction of thee homology vector pSY920 by transient expression In order to determine whether the HCMV/beta-gal homology vector construction was correct and would function when inserted into HCMV, beta-gal expression was tested in a transient expression experiment. In this experiment the homology vector plasmid DNA is introduced into cells followed by superinfection with wild-type HCMV. The vital transacting regulatory signals should activate and allow for beta-gal expression from the plasmid DNA if the beta-gal construction is correct and if the gpX promoter responds to the heterologous HCMV signals.

HFF cells were transfected with plasmid DNA according to the method of Spaere and Mocarski (25). 10 micrograms DNA were suspended in MEM media (plus 100 units/ml penicillin and streptomycin, each 2 mM glutamine, no serum and 200 micrograms/ml DEAE Dextran). DNA was allowed to absorb for 4 hours, the medium was removed and cells were re-fed with the same media, without DEAE Dextran, containing 10% fetal calf serum. 16 hours later the cells were again re-fed. At 48 hours after transfection, the cells were infected at a multiplicity of 10 with HCMV. 10 hours later, the cells were harvested and tested for beta-gal.

Beta-gal assay of infected monolayers: The infected cell monolayers (60 mM dish) were washed in phosphate buffered saline (PBS) and lysed in 0.2 ml PBS containing 1% sodium dodecylsulfate (SDS). The lysate (200 microliters) was diluted into Z buffer (800 microliters) (35), the enzyme substrate (ONPG, 200 microliters) was added and the development of yellow color was monitored at 420 nm (37° C.). As shown in Table 1, pSY920 produced beta-gal in this transient expression test indicating that the construction was correct and functional.

TABLE 1

TRANSIENT EXPRESSION ASSAY
β-GAL ACTIVITY IN LYSATES

| Plasmid | HCMV | Intensity of Enzyme Response | O.D. 420 |
|---|---|---|---|
| pSY920 | + | ++++ | 2.848 |
| PRV gpX/β-gal | − | − | 0.218 |
| HCMV EcoRI H | | | |
| pSY921 | + | +++ | 2.024 |
| HCMV IE/β-gal | − | +/− | 0.286 |
| No plasmid | + | − | 0.228 |
| | − | − | 0.212 |

These results also indicate that the heterologous gpX promoter from pseudorabies is functional in HFF cells and responds well to HCMV regulatory signals. In similar experiments, pSY920 also expresses beta-gal transiently in response to pseudorabies super-infection, as would be expected (Table 2).

TABLE 2

TRANSIENT EXPRESSION ASSAY
β-GAL ACTIVITY IN LYSATES

| Plasmid | Pseudorabies | Intensity of Enzyme Response | O.D. 420 |
|---|---|---|---|
| pSY920 | + | ++ | 1.343 |
| PRV gpX/β-gal | − | − | 0.218 |
| pSY921 | + | + | 0.961 |
| HCMV IE/β-gal | − | +/− | 0.286 |
| No plasmid | + | − | 0.228 |
| | − | − | 0.212 |

1.5 Insertion of PRV gpX/beta,gal into HCMV using DSY920 pSY920 plasmid DNA was combined with HCMV DNA and transfected into HFF cells using the polybrene protocol (Section Id).

In this case a positive stock was selected and plated out. A total of 76 blue plaques were picked of which 58 (76%) gave rise to secondary vital stocks. Of these secondary stocks, 5 (8.6%) were positive by ONPG assay of the supernatants from infected cell cultures. The recombinant virus was further purified through additional rounds of plaque picking.

1.6 Confirmation of recombinant HCMV

The presence and location of the beta-gal gene inserted into HCMV was confirmed by Southern blot analysis. FIG. 3B presents the data from analysis of this recombinant virus containing beta-gal as an insert into the Xho deletion. Lane 1 contains molecular weight markers. Lane 2 contains plasmid pSY1112 DNA digested with EcoRI and used as a control for the PRV gpx/betagal gene. Two fragments of 8.2 kb and 4.4 kb representing both the plasmid sequences and the betagal gene respectively are revealed. Lane 3 contains Towne DNA digested with EcoRI and probed with beta-gal DNA demonstrating that there is no hybridization of the probe to the parent virus. Lane 4 contains DNA from the recombinant virus probed with beta-gal and reveals two fragments H and U that contain the inserted *E. coli* gene. We interpret this result to indicate that homologous recombination has occurred in both the internal junction fragment and one of the terminal repeat fragments that contains the same DNA sequence.

These results indicate that it is possible to delete the Xho region of EcoRI H and to insert and express foreign genes at this point on the HCMV genome. This region is probably permissive for such manipulations due to the presence in the virus genome of an unaltered duplicate of the information contained in this region.

2.1 Construction of a second beta-gal construction, PSY921, for insertion into ECORI H fragment using CMV I.E promoter Our goal is to express a gene coding for anti-sense RNA for HIV in OKT4 lymphocytes and other cells permissive for HIV. HCMV infects OKT4 lymphocytes and expresses at least immediate early (IE) genes in these cells (26,27) and probably replicates as well (28). It was important for our objectives to express a foreign gene under the control of the HCMV IE promoter.

2.2 Beta-gal construction

Summary: The immediate early promoter region of HCMV was cloned and fused to a beta-gal construct which contained the HSV TK poly adenylation signal at the 3' end.

Constructions: We have cloned the 19 kb XbaI E fragment from the long unique region. This fragment contains the IE promoter region (29). A 2.1 kb Pst fragment was sub-cloned from the XbaI piece (see FIG. 4). The Pst fragment includes the IE promoter and enhancer, cap site, the first exon and the first 2 introns up to the AUG protein start.

This enhancer/promoter fragment was fused to a beta-gal fragment containing the following elements. The betagal enzyme is truncated at the 5' end at the BamHI site located 4 amino acids from the amino-terminus. Located at the 5' end of this gene is the promoter region of the RSV TK gene including the protein start codon of TK which is fused in-frame to the beta-gal gene. The Pst-BamHI fragment from the 3' end of the HSV TK gene carrying the poly adenylation signal is located at the 3' end of the beta-gal gene. The IE promoter Pst fragment was joined tO the 5' end of this beta-gal construct at the Pst site of the HSV TK region replacing the HSV TK promoter with the HCMV IE promoter to create pSY921.

2.3 Insertion of HCMV-IE/beta-gal (DSY921) into EcORI H fragment at Xho I deletion (pSY930)

As shown in FIG. 2, the 6.1 kb HCMV IE/beta-gal construction was inserted into the 5.4 kb Xho I deletion region of the EcoRI H (10.2 kb) fragment (see Section 1.3). This construction is pSY930.

2.4 Confirmation of a functional construction of the pSY921 by transient expression As described in Section 1.4, the DNA f tom the HCMV IE/beta-gal plasmid pSY921 was tested in the transient expression system. The plasmid beta-gal gene responded to HCMV signals and expressed the enzyme. In this construction, the IE promoter may produce less enzyme than the gpX promoter in the transient assay system (Tables 1, 2). However, the beta-gal expression was observed to begin sooner after super-infection than did gpX promoted expression. In addition, there was some measurable expression of the beta-gal from the IE promoter in the absence of vital super-infection (see Table 1).

It is interesting to note that pSY921 also expressed beta-gal in this system when pseudorabies was used to super-infect the cells (Table 2). Thus, just as the gpX promoter responded to heterologous regulatory signals when located in HCMV, the IE promoter of HCMV responds to the heterologous signals of pseudorabies.

These results indicated that pSY921 was intact and functional.

2.5 Insertion of HCMV/beta-gal IE into HCMV at EcoRI H using pSY930 pSY930 DNA was combined with HCMV DNA and transfected into HFF cells as described in Section 1.5. A beta-gal positive transfection stock was identified and plated out. Twenty-seven positive plaques were picked from this plating for further purification. Work continues on the further purification of this recombinant virus. However, the preliminary positive results indicate that the IE promoter probably functions to express foreign genes in the EcoRI H location in HCMV. Thus foreign genes can be expressed at this site in HCMV either under control of homologous (IE) or heterologous (gpX) herpesvirus promoters.

3.1 Identification of a second region of HCMV permissive for insertion and expression of foreign genes We are continuing to examine other regions of the HCMV genome in addition to the Xho junction fragment for the insertion and expression of foreign genes. Located within the 19 kb Xba D fragment is a 5.4 kb BamHI fragment containing a portion of the long internal repeat. This fragment expresses 2 mRNA's: a 1.2 kb early message and a major 2.7 kb early message. The 2.7 kb mRNA is the most abundant mRNA produced at both early and late times during infection and maps to about 600 base-pairs upstream of the RI site on this fragment (29).

3.2 Construction of the homology vector pSY1112

This cloned 5.4 kb BamHI fragment was opened at the RI site and the PRV gpX/beta-gal construct (described above (1.2)) was inserted (see FIG. 5). As the integrity of the beta-gal construct had already been established, this new plasmid (pSY1112) construct was not further tested by transient infection but was used directly in homologous recombination.

3.3 Insertion of PRV gpx/beta-gal into HCMV BamHI (5.4 kb) using pSY1112

A number of independent transfection stocks were made in which pSY1112 and HCMV DNA were mixed in-various proportions and transfected in HFF cells using the polybrene method. The results of these transfections are described in Table 3. One stock out of 30 showed higher than expected beta-gal activity (CT3-3) and this was used for the isolation of recombinant virus. A recombinant HCMV was purified from this stock by plaque purification. This recombinant, proved to give the best yield of virus and enzyme among the HCMV recombinants constructed to date. As a result, our initial efforts have been focused on this site for the insertion of foreign genes. This recombinant virus was designated S-HCMV-001. Stocks of this virus typically produced a low level (about 1%) of white plaques when assayed for beta-gal production. These white plaques have not been characterized.

TABLE 3

| Stock | Plasmid | HCMV DNA | Day post CT plaques | harvest | ONPG |
|---|---|---|---|---|---|
| CT3-1 | 1112 0.5 μg | 10–20/ | 14 | 31 | – |
| 2 | | (10/3) | 22 | 32 (D) | ND |
| 3 | | | 31* | 37 | ++++ |
| 4 | | | 14 | 31 | – |
| 5 | 1.0 μg | | — | 32 (D) | ND |
| 6 | | | 22 | 35 | – |
| 7 | | | 31* | 32 | – |
| 8 | | | — | 32 (D) | ND |
| 9 | | no HCMV | — | 32 (D) | ND |
| 10 | no plasmid | no HCMV | — | 32 (D) | ND |
| CT4-1 | 1112 1.0 μg | 15/ | 13 | 20 | – |
| 2 | | (10/3) | 13 | 20 | – |
| 3 | | | 13 | 20 | – |
| 4 | | | 13 | 20 | + |
| 5 | | | 13 | 17 | – |
| 6 | | | 13 | 20 | + |

TABLE 3-continued

| Stock | Plasmid | HCMV DNA | Day post CT plaques | harvest | ONPG |
|---|---|---|---|---|---|
| CT5-1 | 1112 0.5 μg | 20/ | 8 | 16 | + |
| 2 | | (10/3) | 8 | 18 | — |
| 3 | | | 8 | 18 | — |
| 4 | | | 8 | 18 | — |
| 5 | | (12/16) | 12 | 21 | — |
| 6 | | | 8 | 21 | + |
| 7 | | | 8 | 21 | — |
| 8 | | | 12 | 21 | +/— |
| 9 | no plasmid | | — | 16 (D) | ND |
| CT6-1 | 1112 0.5 μg | 5/ | 11 | 15 | +/— |
| 2 | | (12/16) | 11 | 20 | — |
| 3 | | | — | 15 (D) | ND |
| 4 | | 10/ | 11 | 20 | — |
| 5 | | | 7 | 15 | +/— |
| 6 | | | 11 | 15 | +/— |
| 7 | | 20/ | 7 | 20 | +/— |
| 8 | | | 11 | 18 | ++ |
| 9 | no plasmid | no HCMV | — | 15 | ND |

3.4 Confirmation of S-HCMV-001 structure by Southern blot analysis

In FIG. 3A viral DNA was digested with HindIII and probed in a Southern blot with the homologous XbaI M fragment (see FIG. 1 for restriction map) or with beta-gal DNA. When probed with the XbaI M fragment, HindIII fragments E, G, and K from Towne DNA hybridize (lane 2). In the recombinant, both fragments E and G which result from inversion of the unique short region have increased in size due to the insertion of the beta-gal gene, but the K fragment remains the same size (lane 3 and ½ of lane 4). This indicates that the insertion of beta-gal in the junction region in effect freezes the unique long segment of the genome in one orientation and prevents the normal reorganization of the genome that occurs in this region. When the same digested DNA is probed with the beta-gal gene (½ of lane 4 and lane 5), only fragments E and G hybridize, confirming the conclusion reached above. Lane 6 shows that there is no hyridization of beta-gal with the Towne strain DNA as expected.

SUMMARY

We have identified 2 sites on the CMV genome within the internal repeat region which allow deletion and/or insertion of foreign genes and permit the expression of these genes using either heterologous or homologous herpesvirus promoters.

Example 4

DESIGN AND CHEMICAL SYNTHESIS OF DNA CODING FOR HIV ANTI-SENSE RNA

Zamecnik, et al. (30) published a study on the effects of anti-sense RNA on HIV replication in vitro. This work pointed to specific anti-sense RNA's that were effective in blocking HIV replication. Based upon this information, we designed the anti-sense gene. The synthesis of the anti-sense gene is outlined in Table 4.

4.1 Synthesis of DNA oligomers

The two fragments shown in Table 4 were synthesized as follows, using conventional chemical synthesis methods:

TABLE 4

Oligomers Synthesized: (5' to 3')

1-A  AATTGTCGACGCGTACTCACCAGTCGCCGCACACCCAATTCTGAAAATGGTCGAC
1-B  AGCTGTCGACCATTTTCAGAATTGGGTGTGCGGCGACTGGTGAGTACGCGTCGAC

Final Fragments:

Fragment A

5'-AATTGTCGACGCGTACTCACCAGTCGCCGCACACCCAATTCTGAAAATGGTCGAC       -3'
3'-        CAGCTGCGCATGAGTGGTCAGCGGCGTGTGGGTTAAGACTTTTACCAGCTGTCGA -5'
   ----                                                              ----
   R1                                                                Hd3
        ------                                                   ------
        Sal                                                      Sal
              --------------------------
              Splice Donor Site
                                         --------------------
                                         Splice Acceptor Site The N,N-diisopropylphosphoramidites, controlled-pore glass columns and all synthesis reagents were obtained from Applied Biosystems, Foster City, Calif.

Synthetic oligonucleotides were prepared by the phosphite triester method with an Applied Biosystems Model 380A DNA synthesizer using a 10-fold excess of protected phosphoramidites and 1 micromole of nucleotide bound to the synthesis support column. The chemistries used for synthesis are the standard protocols recommended for use with the synthesizer and have been described (31). Deprotection and cleavage of the oligomers from the solid support were performed according to standard procedures as described by McBride (32). The repetitive yield of the synthesis as measured by the optical density of the removed protecting group as recommended by Applied Biosystems (1984) was greater than 97.5%.

The crude oligonucleotide mixture was purified by preparative gel electrophoresis as described by the Applied Biosystems protocols of Nov. 9, 1984 (User Bulletin No. 13). The acrylamide gel concentration varied from 10 to 20% depending upon the length of the oligomer. The purified oligomer was identified by UV shadowing, excised from the gel and extracted by the crush and soak procedure (33).

The fragments 1-A and 1-B were mixed (50 ng of each), heated to 65° C. and allowed to anneal by slowly cooling at room temperature (10 min at 55° C., 10 min at 47° C., 10 min at 42° C., 10 min at 37° C., and 10 min at room temperature). The annealed DNA was ligated into vector pBS M13+ (from Stratagene) cut with EcoRI and HindIII and transformed into JM109. Colonies were screened by colony hybridization using p$^{32}$ labeled fragment 1-A. Thirty positive clones were selected, DNA was isolated from the colonies (mini prep method) and examined by agarose gel electrophoresis for inserts. The DNA inserts of 6 plasmids were sequenced by the primer extension method for double stranded DNA's (34). Clone BSI-32 (pSY1157) was shown to contain the correct A fragment sequence and was selected for further manipulation.

The A fragment was engineered for ultimate placement into an HCMV homology vector in such a way that its expression would be controlled by the HCMV IE promoter and the presence of the inserted gene could be detected in HCMV by expression of beta-gal. The initial constructs involved placing fragment A downstream from the IE HCMV promoter and upstream of beta-gal so that antisense RNA synthesis would occur when beta-gal expression was observed. The first step in this procedure was to construct and test an improved new HCMV IE promoter-beta-gal vector (pSY1132).

4.2 Construction of pSY1132

The PstI fragment containing the HCMV IE promoter enhancer region (FIG. 4 and Section 2.2) was cut at the internal SacI site to create a 1.1 kb fragment carrying the IE promoter and enhancer and part of the first intron, including the cap site. This shortened IE promoter fragment was then linked to the beta-gal gene using a fragment of herpes simplex thymidine kinase (HSV TK) gene to supply the untranslated 5' end of the mRNA. The RsaI fragment at the 5' end of HSV TK was coupled to BamHI linkers and joined to the 5' end of the BamHI beta-gal fragment (described above, Section 2.2). This construction contains 6 additional amino acids, 3 from the 5' end of the TK structural gene and 3 from the BamHI linker (see FIG. 6). The beta-gal carries the HSV TK gene polyadenylation signals at the 3' as described (Section 2.2). The Pst-Sac IE HCMV fragment is inserted at the cap site of the HSV TK segment (FIG. 6) to create pSY1132.

4.3 Confirmation of a functional construction by transient expression psY1132 was tested in the transient expression system (Table 5). Plasmid pSY844 (see Section 1.1) served as a positive control in these assays.

TABLE 5

Transient Expression of the AIDS Anti-sense Sequence

| Plasmid | HCMV | Intensity of Enzyme Response | O.D. 420 |
| --- | --- | --- | --- |
| pSY1132 | + | ++++ | 2.8301 |
| HCMV IE/β-gal | + | ++++ | 2.8247 |
|  | + | ++++ | 2.8219 |
|  | − | +/− | 0.1049 |
| pSY844 | + | ++ | 0.8621 |
| PRV gpX/β-gal | + | ++ | 0.7319 |
|  | + | ++ | 1.0014 |

TABLE 5-continued

Transient Expression of the AIDS Anti-sense Sequence

| Plasmid | HCMV | Intensity of Enzyme Response | O.D. 420 |
| --- | --- | --- | --- |
|  | − | − | −0.0481 |
| pSY1159 | + | + | 0.2384 |
| HCMV IE/AIDS/β-gal | + | + | 0.1816 |
|  | + | + | 0.2026 |
|  | − | − | −0.0529 |
| pSY1160 | + | +/− | 0.1166 |
| HCMV/IE/AIDS/β-gal | + | +/− | 0.1469 |
|  | + | +/− | 0.1457 |
|  | − | − | −0.0036 |
| No plasmid | + | − | −0.0211 |
|  | − | − | −0.0460 |

Infected cell monolayers were washed in PBS and lysed in PBS containing 1% non-ionic detergent (NP40). An aliquot of the lysate (100 microliters) was diluted into (700 lambda) Z buffer and assayed as described previously.

The results from these assays indicate that pSY1132 is intact and functional. In addition, this construct with the truncated HCMV IE promoter/enhancer fragment is the most active of the herpes promoter beta-gal fusions so far tested (compare to pSY844). As in the case of pSY921 (carrying the larger HCMV IE fragment), the plasmid DNA was capable of some slight beta-gal expression in the absence of CMV super-infection.

4.4 Construction of anti-sense RNA gene: beta-gal fusion vectors (DSY1159 and 1160)

The initial construction of the anti-sense homology vector involved insertion of the anti-sense gene from pSY1157 (see Section 4.1) into the BglII site preceding the beta-gal gene in pSY1132. In order to achieve this the fragment A construction was cut from pSY1157 with SalI and the 45 basepair Sal insert was purified from a 3% low melting point agarose gel. The vector pSP72 (a derivative of pSP64) was cut with SalI in the multiple cloning site downstream of the SP6 promoter and was ligated to the purified A fragment. This construction (pSY1158) places the anti-sense RNA gene into a multiple cloning site with unique BamHI sites flanking the construct. The insert was then cut from the plasmid with BamHI and the purified insert DNA, now with BamHI ends, was ligated into the BglII site of pSY1132 within the HSV TK region immediately upstream from the beta-gal 5' end and downstream from the HCMV IE promoter/enhancer. The insertion of the anti-sense fragment occurred in 2 orientations, the "correct" anti-sense orientation relative to the promoter (pSY1159) and in the "incorrect" sense orientation (pSY1160).

The constructions pSY1159 and 1160 were confirmed by double-stranded dideoxy sequencing and by restriction analysis.

4.5 Effect of anti-sense gene insertion on beta-gal construction: transient expression assay pSY1159 and 1160 were tested in the transient expression assay system (Table 5). When the anti-sense sequence is present in the (correct) anti-sense orientation (pSY1159), the downstream beta-gal gene is expressed at-low levels in the system. However, when the sequence is in the opposite orientation at the same location (pSY1160), even less beta-gal is detected. It is not clear why the anti-sense sequence affects the expression level of beta-gal and work is under way to investigate this phenomenon.

4.6 Constructions to improve the level of anti-sense expression pSY1159 and 1160 do produce measurable beta-gal in transient expression. However, before preceding to insert the anti-sense gene into HCMV better expression of the gene is desirable. We have shown that some genes or DNA sequences when fused to the N-terminal of beta-gal severely depress beta-gal expression. When these same sequences are fused to the C-terminal of beta-gal, much higher levels of expression are permitted upon infection with the recombinant pseudorabies.

The AIDS antisense gene has been placed behind beta-gal as a carboxy fusion and the expression level has been raised dramatically.

Summary: Anti-Sense RNA gene constructions:

We have constructed a 50 basepair anti-sense RNA gene from HIV based upon published data indicating that this sequence is effective in vitro in blocking HIV replication. The anti-sense RNA gene has been placed under the control of a strong IE HCMV promoter/enhancer sequence and beta-gal expression has been engineered as a marker for anti-sense RNA expression. With the antisense RNA fused to the carboxy terminis of B-gal, the expression level of RNA and protein is good.

Example 5

INFECTION OF HUT78 CELLS IN VITRO WITH RECOMBINANT HCMV AND EXPRESSION OF A FOREIGN GENE

In order to deliver the AIDS anti-sense RNA to target OKT4 cells using our strategy, HCMV must be able to infect these cells and actively transcribe RNA from the immediate early promoter. A recent report (28) describes the replication of HCMV AD169 in T-lymphocytes. The demonstration of infected cells and increases in vital titer were presented as evidence for infection. These data appear to show-that both OKT4 $^+$and OKT8$^+$subpopulations can support HCMV replication. The presence of immediate early transcripts from HCMV in infected OKT4 $^+$cells has also been demonstrated (26). In the experiments reported here, we have used recombinant HCMV containing the beta-gal cassette inserted at the RI site in the BamHI fragment of the Towne strain. This virus, designated Strain 001, was chosen because it could be easily detected by blue plaque assay or by beta-gal enzyme determinations. In this virus the beta-gal gene is controlled by the PRV gpX beta-gal promoter as described in Sections 3.1–3.4. We have also used Towne, AD169, and "Jerry" but with these viruses plaques must be quantitated by the standard plaque assay. We have used three different assays to monitor the infection of the OKT4 cell line HUT-78 with HCMV (as described in Section II, "Infection of OKT4 $^+$Lymphocytes by HCMV").

The results of our experiments are shown in Table 6.

TABLE 6

Infection of OKT4$^+$ Cells with HCMV a) Infectious Center Assay (% Infectious Centers)

| Virus | Days Post Infection | | | | | |
|---|---|---|---|---|---|---|
| | 3 | 5 | 7 | 10 | 12 | 14 |
| 001 | 0.01 | 0.1 | 0.03 | 0.0 | 0.0 | 0.0 |
| Towne | 0.01 | 1.3 | 0.3 | 0.003 | 0.0 | 0.0 |
| AD169 | 0.02 | 1.8 | 0.56 | 0.007 | 0.0 | 0.0 |
| Jerry | 0.02 | 0.0 | 0.0 | 0.0 | 0.0 | 0.0 |
| no virus | 0.0 | 0.0 | 0.0 | 0.0 | 0.0 | 0.0 |

TABLE 6-continued

Infection of OKT4$^+$ Cells with HCMV b) Cell Free Virus Titer (PFU/10$^5$ cells)

| Virus | Days Post Infection | | | | |
|---|---|---|---|---|---|
| | 4 | 6 | 8 | 11 | 14 |
| 001 | 20 | 200 | 4.8 | 0 | 0 |
| Towne | 600 | 670 | 50 | 0 | 0 |
| AD169 | 350 | 1300 | 200 | 6 | 0 |
| Jerry | 29 | 21 | 0 | 0 | 0 |
| no virus | 0 | 0 | 0 | 0 | 0 |

$$\% \text{ Infectious Centers} = \frac{(\# \text{ of plaques})(\text{dilution factor})(100)}{(\# \text{ of cells/ml of undiluted culture})(\text{ml culture plated})}$$

Both the infectious center assay (a) and the assay of cell free virus (b) indicate that HCMV is capable of infecting HUT-78 cells. The infectious center assay indicates that the maximum number of infected OKT4 cells (maximum of 1.8% in this experiment) is observed 5–7 days post infection. AD169 leads to more infected cells than does Towne which in turn leads to more than its. recombinant, 001, containing the beta-gal gene of *E. coli*. Strain "Jerry", the clinical isolate, failed to produce significant infectious centers in this cell line. These data are supported by the cell free virus titers-produced from infected HUT-78 cultures (Table 6b). The highest virus titers were observed in AD169 infected cells about 1 week after infection. Lower titers were obtained for the Towne strain and even lower for 001. Titers for strain "Jerry" did not increase during the experiment.

Establishing the infection of various lymphocyte cell types by HCMV is complicated by the carryover of the inoculum virus prepared as a crude cell lysate. In our experiments, the crude cellular lysate contains not only virus but considerable amounts of beta-gal activity. This activity was sufficiently high and stable as to mask any activity produced by OKT4 cells infected with 001. The results presented in Table 5 should not be affected by the carryover of material from the inoculum. Rising virus titers and increasing infectious centers indicate active infection. In subsequent experiments we are using cell-free virus preparations and are taking samples at zero time immediately after infection and absorption to better control any potential variables.

References

1. B. Roizman, in "The Herpesviruses Vol 1", B. Roizman ed,, pp, 1–23, Plenum Press, N.Y., 1982.
2. E. Gold and G. A. Nankervis, in "Vital Infections of Humans: Epidemiology and Control", A. S. Evans, ed., pp. 143–161, Platenum Press, N.Y., 1976.
3. S. Elek and H. Stern, Lancet 1:1–5, 1974.
4. B. J. Neff, et al., Proc. of the Soc. for Exptl. Biol. and Med. 160:32–37, 1979.
5. S. A. Plotkin, et al., Journal of Infectious Disease 134:470–475, 1976.
6. M. Just, et al., Infection 3:111–114, 1975.
7. R. C. Gehrz, et al., Arch. Intern. Med. 140: 936–939, 1980.
8. J. P. Glaser, et al., Ann. Intern. Med. 91: 676–683, 1979.
9. G. V. Quinnan Jr., et al., Ann. Intern. Med. 101: 478–483, 1984.
10. T. Maniatis, et al., Molecular Cloning: A Laboratory Manual, Cold Spring Harbor Laboratory Press, 1982.

11. D. M. Knipe, et al., Proc. Natl. Acad. Sci. USA 75: 3896–3900, 1978.
12. E. S. Mocarski, et al., Cell 22: 243–244, 1980.
13. L. E. Post, et al., Cell 24: 555–565, 1981.
14. L. E. Post and B. Roizman, Cell 25: 227–232, 1981.
15. K. L. Poffenberger, et al., Proc. Natl. Acad. Sci. USA 80:2690–2694, 1981.
16. M. G. Gibson and P. G. Spear, Journal of Virology 48:3 96–404 1983.
17. G.T.-Y. Lee, et al., Proc. Natl. Acad. Sci. USA 3:6612–6616, 1982.
18. M.-F. Shih, et al., Proc. Natl. Acad. Sci. USA 81:5867–5870, 1984.
19. R. Desrosiers, et al., Ninth Annual Herpesvirus Meeting, Seattle, Abstract #280, 1984.
20. M. Arsenakis and B. Roizman, in "The High Technology Route to Virus Vaccines", American Society for Microbiology, Washington, D.C. 1985 (Proceedings of the First Annual Southwest Foundation for Biomedical Research International Symposium, Houston, Texas, 8–10 November, 1984).
21. L. E. Post, et al., Tenth International Herpesvirus Workshop, Ann Arbor, Michigan, August, 1985.
22. R. S. Lowe, et al., Proc. Natl. Acad. Sci. USA 84:3896–3900, 1987.
23. Wong-Staal, F. and R. C. Gallo, Nature 317:395–403, 1985.
24. J. E. Gottenberg, et al. J. Exp. Med. 154, 1403–1418, 1981.
25. R. R. Spaete and E. M. Mocarski, J. Virol. 56:135–143, 1985.
26. G. P. A. Rice, et al., Cytomegalovirus Infects Human Lymphocytes and Monocytes: Virus Expression is Restricted to Immediate-Early Gene Products, Proc. Natl. Acad. Sci. USA 81:6134–6138, 1984.
27. R. D. Schrier, et al., Science 230:1048–1051, 1985.
28. R. W. Braun and H. C. Reiser, Replication of Human Cytomegalovirus in Human Peripheral Blood T Cells, J. Virol. 60:29–36, 1986.
29. D. R Thomsen, et al., Proc. Natl. Acad. Sci. USA 81:659–663, 1984.
30. P. C. Z amecnik, et al., Proc. Natl. Acad. Sci. USA 83:4143–4146, 1986.
31. Matteuchi, et al., Journal Amer. Chem. Soc. 103:3185–3319, 1981.
32. McBride, et al., Tetrahedron Letters 24:245–248, 1983.
33. Smith, Methods in Enzymology, 65:371–379, 1980.
34. R. J. Zagursky, et al., Anal. Techn. 2:89–94, 1985.
35. J. H. Miller, (ed), Experiments in Molecular Genetics, Cold Spring Harbor, NY, pp. 352–355, 1972.

What is claimed:

1. A recombinant human cytomegalovirus which comprises a foreign DNA sequence inserted within the genomic DNA of human cytomegalovirus, wherein the foreign DNA sequence is inserted within the 5.4 kb BamHI fragment shown in FIG. 1 or within the 5.4 kb XhoI fragment shown in FIG. 2, and wherein the foreign DNA sequence is capable of being expressed in a host cell infected with the recombinant human cytomegalovirus.

2. The recombinant human cytomegalovirus of claim 1, wherein the foreign DNA sequence is inserted into the human cytomegalovirus genome at the EcoRI restriction endonuclease cleavage site of the 5.4 kb BamHI fragment shown in FIG. 1.

3. The recombinant human cytomegalovirus of claim 1, wherein the foreign DNA sequence is inserted into the human cytomegalovirus genome so as to replace the 5.4 kb XhoI fragment shown in FIG. 2.

4. The recombinant human cytomegalovirus of claim 1, wherein the foreign DNA sequence encodes a human immunodeficiency virus anti-sense mRNA sequence.

5. The recombinant human cytomegalovirus of claim 4, wherein the foreign DNA sequence comprises the nucleotide sequence
5'-GCGTACTCACCAGTCGCCGCACAC-CCAATTCTGAAAATGG-3'
3'-CGCATGAGTGGTCAGCGGCGTGTGGGT-TAAGACTTTTACC-5'.

6. The recombinant human cytomegalovirus of claim 1, wherein the foreign DNA sequence encodes an antigenic polypeptide.

7. The recombinant human cytomegalovirus of claim 6, wherein the foreign DNA sequence encodes a malarial surface antigen.

8. The recombinant human cytomegalovirus of claim 1, wherein the foreign DNA sequence encodes *E. coli* b-galactosidase.

9. The recombinant human cytomegalovirus of claim 1, wherein the expression of the foreign DNA sequence is under control of an upstream human cytomegalovirus promoter.

10. The recombinant human cytomegalovirus of claim 9, wherein the upstream human cytomegalovirus promoter is the immediate early promoter.

11. The recombinant human cytomegalovirus of claim 1, wherein the expression of the foreign DNA sequence is under control of a heterologous upstream promoter.

12. The recombinant human cytomegalovirus of claim 11, wherein the heterologous upstream promoter is the pseudorabies glycoprotein gpX promoter.

* * * * *